United States Patent [19]

Cengel et al.

[11] 4,086,251

[45] * Apr. 25, 1978

[54] PROCESS FOR MANUFACTURING POLYALKENYL SUCCINIC ANHYDRIDES

[75] Inventors: John A. Cengel, Wheaton; Imre Puskas, Glen Ellyn, both of Ill.

[73] Assignee: Standard Oil Company (Indiana), Chicago, Ill.

[*] Notice: The portion of the term of this patent subsequent to Dec. 16, 1992, has been disclaimed.

[21] Appl. No.: 673,707

[22] Filed: Apr. 5, 1976

Related U.S. Application Data

[63] Continuation-in-part of Ser. No. 548,382, Feb. 10, 1975, abandoned.

[51] Int. Cl.$^2$ ............................................ C07D 307/60
[52] U.S. Cl. ................................................. 260/346.74
[58] Field of Search ................................ 260/346.8 R

[56] References Cited
U.S. PATENT DOCUMENTS

| | | | |
|---|---|---|---|
| 3,202,679 | 8/1955 | Andrewsen et al. | 260/346.8 |
| 3,231,587 | 1/1966 | Rense | 260/346.8 |
| 3,412,111 | 11/1968 | Irwin | 260/346.8 |
| 3,476,774 | 11/1969 | Taweski et al. | 260/346.8 |
| 3,927,041 | 12/1975 | Cengel et al. | 260/346.8 |
| 3,935,249 | 1/1976 | Cengel et al. | 260/346.8 |
| 3,960,900 | 6/1976 | Puskas et al. | 260/346.8 |

*Primary Examiner*—Henry R. Jiles
*Assistant Examiner*—Bernard Dentz
*Attorney, Agent, or Firm*—Mark DiPietro; Arthur G. Gilkes; William T. McClain

[57] ABSTRACT

A process for producing alkenyl substituted anhydrides which comprises introducing one mole of polypropene or polybutene having a number average molecular weight of 200–3000, 0.8–5.0 moles of the anhydride of an unsaturated dicarboxylic acid and 5–200 ppm of an additive which suppresses the formation of tarry materials and undesirable reaction side products and/or improves yield, into a reaction zone, reacting said materials at a temperature from about 150° C to about 300° C to form the alkenyl anhydride, distilling off and condensing the unreacted anhydride from the reaction mixture, recovering the alkenyl substituted anhydride, and returning at least a portion of the recovered unreacted anhydride to a reaction zone for reaction with an alkenyl material.

9 Claims, No Drawings

PROCESS FOR MANUFACTURING POLYALKENYL SUCCINIC ANHYDRIDES

PRIOR APPLICATIONS

This application is a continuation-in-part of U.S. Ser. No. 548,382, filed Feb. 10, 1975 and now abandoned.

BACKGROUND OF INVENTION

Viscous polybutenes of about 200 to about 3000 $\overline{M}_n$ have viscosities in the range of about 4 to about 5500 centistokes at 100° C. Such polybutenes are commercially available from polymerization of refinery butenes; isobutylene, cis-butene-2 and butene-1 are generally present with butane in a $C_4$ fraction. Commercially since about 1940, such $C_4$ fractions with or without added isobutylene, or isobutylene rich concentrates have been polymerized in the presence of Friedel-Crafts catalyst. The wide range in viscosity, and in molecular weight depends, as is known, on polymerization temperature, to a lesser extent on catalyst and its concentration, and on the olefin content of the feed. The viscous polybutenes are essentially water white and thermally decompose with no residue at temperature above 275° C and have some use applications in engine oils as anti-scuff agents and viscosity index improvers and in fuels for internal combustion engines to reduce or suppress deposits in the fuel induction systems.

The viscous polybutenes have also found use as components of caulking compounds, adhesives and electric-cable insulating oils. However, the greatest use of the viscous polybutenes is as a raw material in the manufacture of addition agents for fuels and gasoline because the viscous polybutenes are reactive olefins and provide branched-chain alkyl structure in derivatives enhancing their solubility in petroleum products such as lubricant oils, fuels and refinery streams. The derivatives of most interest in the past 15 years are from the polybutenyl-substituted intramolecular anhydrides of aliphatic dicarboxylic acids such as succinic anhydride. The polybutenyl-substituted saturated aliphatic anhydrides have been used per se, or as diesters, amides, imides, amidines, imidines, and neutral or overbased basic metal salts as addition agents in petroleum products. The addition agents from polybutenes of $\overline{M}_n$ below 500 are mainly used in fuels; for example in gasoline to inhibit rusting, carburetor deposits, and carburetor icing and in diesel fuels to inhibit rust, corrosion and smoke, and in motor oils and industrial oils as rust and wear inhibitors.

The addition agents from polybutenes of 500 to about 3000 $\overline{M}_n$ have found extensive use as detergent-dispersants in motor oils and lesser use as carburetor detergents in gasoline, heat exchanger antifoulants in refinery streams, rust and corrosion inhibitors in surface coatings and as emulsifiers and demulsifiers.

The viscous polybutenes are complex mixtures of polymers, copolymers and interpolymers of isobutylene, cis-butene-2 and butene-1. The nature and relative amounts of the butene monomers involved in the polymerization leading to a particular $\overline{M}_n$ polybutene are not indicative of the resulting polymer product because extensive isomerization occurs during polymerization. The viscous polybutenes, although largely monoolefins, may contain 0 to 20% isoparaffins. The unsaturation in the viscous polybutene molecules is predominantly in a terminal or near terminal group which, as later illustrated, are of the trisubstituted or vinylidene type. The non-olefinic chain portion of the polybutene molecules is composed of normal butyl and isobutyl monomer units and hence is a long and branched alkyl chain. Such long, branched alkyl chain of the lighter (below 500 $\overline{M}_n$) polybutenes contain relatively greater amounts of normal butyl units and lesser amounts of isobutyl units. The heavier (500–3000 $\overline{M}_n$) polybutenes contain relatively greater amounts of isobutyl units and lesser amounts of normal butyl units which are concentrated near the end of the long, branched alkyl chain. For example, the structures of a polydisperse polybutene of about 900 $\overline{M}_n$ made with $AlCl_3$ catalyst have in part been identified through the use of infrared spectroscopy (calibrated by NMR) and permanganate cleavage. The principal olefin structures identified are shown below

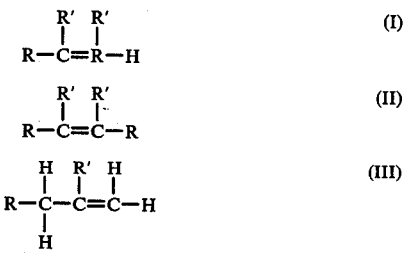

wherein R is the long, branched alkyl chain, R' is mainly methyl and the ratio of iso-$C_4$ to n-$C_4$ is about 3:1.

With respect to polybutene addition reactivity with unsaturated intramolecular anhydrides, it is believed, that the olefinic terminal groups in the three structures shown above are in the decreasing reactivity order of III, I and II. In the uncatalyzed addition reaction, which is an equilibrium reaction, some of the slower reacting molecular species remain unreacted and with the isoparaffinic polymer species (0–20% of the total polymer product) which do not react at all, the desired polybutenyl-substituted saturated anhydride product is usually obtained in 50–75 mole % yields.

Such addition reaction between the viscous polybutene and intramolecular anhydride of unsaturated aliphatic dicarboxylic acid can typically use any one of maleic anhydride, citraconic anhydride, itaconic anhydride, ethyl maleic anhydride, halo (e.g., chloro-) maleic anhydride, and the like according to U.S. Pat. Nos. 2,628,942 and 2,634,256 among others. The addition reactions are, in general, conducted at temperatures in the range of 150° to 300° C using polybutene to anhydride molar ratios of reactants in the range of 1.0:0.8–15, generally 1.0:1.05–1.15. In addition to the non-reaction of some olefinic species of polybutene and isoparaffinic entities thereof amounting to a total of up to 40-50% of the polybutene charged, there is also a problem with respect to thermal decomposition and polymerization of the unsaturated anhydride reactant at temperatures upward from 150° C.

Thermal decomposition at temperatures upward from 150° C of unsaturated aliphatic dicarboxylic acids and their anhydrides (e.g. maleic and its anhydride) has been known and is reported, for example in U.S. Pat. No. 3,476,774 which gives earlier documentation sources thereof. Such thermal decomposition is accompanied by evolution of water vapor and oxides of carbon, in a closed reaction vessel, is accompanied by an increase in internal pressure. Under some observed conditions the thermal decomposition can be so substantially instantaneous as to be explosive. In the absence of explosive thermal decomposition a carbon-containing residue is also formed in addition to water vapor and oxides of carbon. Anhydrides can react with the water to form the dicarboxylic acids and then isomerize to the trans form (which is insoluble in the system) or to polymerize. Such thermal decomposition and attendant isomerization or polymerization of the unsaturated anhydride reactant has been observed as occurring during its addition reaction with polymeric olefins, e.g. polybutenes and others, in a closed reaction vessel. There is the increase of internal pressure by involved water vapor and oxides of carbon (mainly $CO_2$) but the attendant carbon-containing residue varies in nature from somewhat granular when the decomposition is only slight to a tarry material mainly adhering to internal surfaces of the reaction vessel when the decomposition is more extensive but well below explosive magnitude. The granular type residue amounts to from about 0.1 to about 0.3 weight percent of the total charge is generally dispersed in the alkenyl-substituted saturated anhydride addition compound product diluted with unreacted components of the olefin polymer, and is readily separated therefrom by filtration. However, the tarry residual, product, which for the most part fouls the internals of the reaction vessel can be as high as 2-3 weight percent of the total charge. The tarry residual material not adhering to reactor internals fouls the filter and interferes with filtration of the desired reaction product. Both types of residue are undesirable because of the above noted fouling characteristics and because their formation results in yield reduction of the desired alkenyl-substituted anhydride addition product.

Generally after a commercial anhydride-alkene reaction, unreacted anhydride is stripped from the reaction product and discarded because it is impure due to the undesired side reactions and would result in low yields if used for further reaction. Purification of the recovered anhydride is generally economically unattractive. The wasted anhydride not only adds to operating costs but also presents a disposal problem.

U.S. Pat. No. 3,202,679 does describe a process for preparing alkenyl succinic anhydrides whereby unreacted maleic anhydride is recovered and recycled. This reference explains that water derived from the decomposition of maleic anhydride hydrolyzes a portion of the maleic anhydride to maleic acid. By using certain process conditions, the maleic acid is isomerized to fumaric acid. Unreacted maleic anhydride is distilled off for recycle and the reaction product is diluted with oil and then filtered to remove insoluble impurities such as fumaric acid. This process does not reduce maleic anhydride decomposition, but only prevents some of the decomposition products from contaminating the recovered maleic anhydride. Another drawback of this process is the additional processing step of separating the fumaric acid from the alkenyl succinic anhydride product.

The improved process disclosed herein produce high yields of alkenyl substituted anhydrides while substantially diminishing the amount of anhydride waste. Decomposition of anhydride and formation of undesirable by-products is minimized, hence unreacted, recovered anhydride and reaction product contamination is also minimized without additional processing steps.

The term "tar and side product suppressing additive" shall be used to describe a chemical compound which inhibits the formation of tarry residual matter and undesirable reaction side products of maleic anhydride and/or increases yield in the reaction of maleic anhydride with propene or butene polymers having a molecular weight from about 200 to about 3000 at a temperature from about 150° C to about 300° C to form a substituted succinic anhydride when said additive is present during the reaction between the polymer and the anhydride at a concentration of 5 to 200ppm based on polymer.

SUMMARY OF INVENTION

This invention provides an improved process for the reaction of polymeric alkenyl and intramolecular anhydrides of mono unsaturated alkylene dicarboxylic acids. In this process one mole of polymeric alkene having a number average molecular weight from about 200 to about 3000, 0.8 to 10 moles of intramolecular anhydride of mono-unsaturated alkylene dicarboxylic acid and an effective amount, generally, 5 to 200 ppm based on polymer, of one or more "tar and side product suppressing additives" are introduced into a reaction zone. These materials are reacted at a temperature from about 150° C to about 300° C to form alkenyl anhydride. Unreacted anhydride and preferably also the additive and its decomposition products are distilled from the reaction mixture and condensed. The alkenyl substituted anhydride is recovered and at least a portion of the recovered unreacted anhydride is returned to a reaction zone for further reaction with said polymer. This process produces high yields of alkenyl substituted anhydrides with minimum anhydride waste.

The polymeric alkenyl materials used are propene or butene polymers having a number average molecular weight from about 200 to about 3000. Polybutene having a number average molecular weight from about 300 to about 2200 is preferred because of commercial availability. Polybutene having a molecular weight of from about 700 to about 1200 is especially preferred because this polymer is often combined with maleic anhydride to form a substituted succinic anhydride which is useful intermediate in the production of various additives for lubricating oils, automotive fuels, and the like. Other intramolecular anhydrides of mono-unsaturated alkylene dicarboxylic acids can also be used such as citraconic, itaconic, ethyl maleic, halo maleic, and the like and also mixtures thereof.

The "tar and side product suppressing additives" inhibit the formation of tarry residual material and undesirable reaction side products of maleic anhydride and/or improve yield in the reaction of maleic anhydride with propene or butene polymers, having a molecular weight from about 200 to about 3000, at a temperature from about 150° C to about 300° C when said additives are present during the reaction between the polymer and the anhydride at a concentration of 5 to 200 ppm based on polymer. The mechanism by which these additives function is not well understood and shall not be speculated upon at this time. But it is known that many of the additives decompose during the alkene-anhydride reaction and may provide small amounts of halogen or halogen radical in the reaction mixture. These additives are high effective when incorporated into the reaction mixture at a concentration from about 5 to about 200 ppm based on polyolefin. While higher concentrations may also be effective, it is unnecessary to add more than about 5 to about 200 ppm additive. The nature and use of certain of these types of additives are described in U.S. Ser. No. 358,911, filed May 10, 1973, granted May 4, 1976, as Pat. No. 3,954,812, U.S. Ser. No. 358,958, filed May 10, 1973, granted Apr. 27, 1976, as Pat. No. 3,953,475; U.S. Ser. No. 358,914, filed May 10, 1973, granted Jan. 27, 1976, as Pat. No. 3,935,249; U.S. Ser. No. 358,915, filed May 10, 1973, granted June 1, 1976, as Pat. NO. 3,960,900; U.S. Ser. No. 402,487, filed Oct. 1, 1973, granted Dec. 16, 1975, as Pat. No. 3,927,041 which disclosures are hereby incorporated by reference into this disclosure and made a part thereof.

A number of different types of compounds are effective as such "tar and side product suppressing additives". One type is chlorinated and/or brominated aliphatic hydrocarbons or their halogenated derivatives. Such aliphatic hydrocarbons may be alkane, alkene, alkyne, or mixtures thereof. Typical, but not all inclusive of such compounds are:

Cl and/or Br-containing aliphatic hydrocarbons such as ethyl bromide, n-propyl chloride, n- and isopropyl bromide, methylene chloride, methylene bromide, chloroform, bromoform, carbon tetrachloride, carbon tetrabromide, ethylene chloride, ethylene bromide, ethylidene chloride, ethylidene bromide, bromochloroethane, trichloroethane, tribromoethane, tetrachloroethane, tetrabromoethane, bromotrichloromethane, bromotrichloroethane, dibromodichloroethane, tetrachloroethylene, trichlorobutanes, tribromobutanes, bromochlorobutanes, bromobutanes, dibromobutanes, dibromochlorobutanes, dichlorobromobutanes, hexachloropropene, and others.

Another type of "tar and side product suppressing additive" is chlorine and/or bromine containing derivatives of carboxylic or sulfonic acids, or N-chloro or N-bromo amides or imides of such acids. Typical, but not all inclusive of such compounds are:

chloracetic acid, acetyl chloride, chloroacetyl chloride, N-chloroacetamide, bromoacetic acid, acetyl bromide, N-bromoacetamide, N-bromo-bromoacetamide, adipyl chloride, adipyl bromide, sebacyl chloride, sebacyl bromide, alpha-chloroadipic acid, alpha-bromo-adipic acid, N-bromo-adipamide, alpha-chloroadipoyl chloride, alpha-bromadipoyl bromide, 2-bromostearic acid, N-bromostearamide, maleyl dibromide, N-bromo-succinicimide, benzoyl chloride, benzoyl bromide, toluoyl chloride, toluoyl bromide, N-bromobenzamide, N-chlorophthalimide, N-bromophthalimide, $N_1$, $N_2$-dibromoterephthalamide, benzenesulfonyl chloride, benzenesulfonyl bromides, N-bromobenzenesulfonamide, toluenesulfonyl chlorides, toluenesulfonyl bromides, N-chlorotoluenesulfonamides, N-bromotoluenesulfonamides, and the like.

Another type of "tar and side product suppressing additive" is chlorinated and/or brominated intramolecular anhydrides of aliphatic carboxylic acids such as chloromaleic anhydride, bromomaleic anhydride and bromosuccinic anhydride, and others.

Still another type of "tar and side product suppressing additive" is chlorinated and/or brominated aliphatic or aromatic ketones and acetals. Typical but not all inclusive of such compounds are:

(A) The halo-ketones typically are alpha-chloro or bromo ketones and di(alpha-chloro- or bromo) ketones. The former include mono, di- and tri-alpha chloro- or bromo-acetone; mono- and di-alpha chloro- or bromo-methylethyl ketone, diethyl ketone, methylpropyl ketone, ethylpropyl ketone, ethylisopropyl ketone, diisopropyl ketone, di-n-propyl ketone, methyl n-butyl ketone, ethyl isobutyl ketone, methyl tert.butyl ketone, n-butyl isopropyl ketone, n-propyl isobutyl ketone, n-propyl tert.butyl ketone, di-n-butyl ketone, diisobutyl ketone, etc. of the symmetrical and mixed alkyl ketones having in addition to the keto carbonyl carbon up to a total of twenty carbon atoms. The alpha-chloro- or bromo-alkyl diketones are those having two keto-carbonyl carbons in a chain of carbon atoms which are otherwise alkyl as in a chain of 4 to 22 carbon atoms wherein the chlorine or bromine atom or atoms is attached to a chain carbon adjacent to a keto carbonyl carbon. Such alpha chloro-or bromo-diketones are illustrated by 1,4-dichloro or dibromo-2,3-butanedione; 1,5-dichloro or dibromo-3,3-dimethyl-2,4-pentanedione; 2,6-dichloro or dibromo-4,4-dimethyl-3,5-hexanedione; 2,6-dichloro or dibromo-4,4-dimethyl-3,5-heptanedione; 1,4-dichloro- or dibromo-2,3-pentanedione; 2,5-dichloro- or dibromo-3,4-hexanedione, and the like. The alpha-chloro- or bromo aromatic ketones are preferably mixed alkyl aryl ketones with the chlorine or bromine on the alpha alkyl carbon as in alpha-chloro or alpha-bromo acetophenone, alpha-chloro- or alpha-bromo acetonaphthone, and the like.

(B) The alpha-chloro or alpha-bromo acetals are preferably $C_1$-$C_{10}$ dialkyl acetals of alpha-chloro- or alpha-bromo- acetaldehyde because the acetaldehyde acetals are more available than acetals of other aldehydes. Of such preferred alpha-chloro or alpha-bromo-acetyl dehyde diethyl acetals are most preferred.

Still another type of "tar and side product suppressing additive" is 1,3 dibromo-5,5-dialkyl substituted hydantoin. A typical example has methyl or ethyl alkyl groups. These are derivatives of hydantoic acid which is a carboxylic acid.

Still another type of "tar and side product suppressing additive" is the group of inorganic acids and salts consisting of dry halogen chloride, calcium bromide and iodine mono chloride, etc.

Still another type of "tar and side product suppressing additive" is the group consisting of chlorine, bromine and iodine.

Some "tar and side product suppressing additives" which are quite suitable in addition to the preferred additives are:

(a) 1,3-dibromo-5,5-dialkyl-substituted hydantoin wherein the alkyl- substituents have a total of 2 to 21 carbon atoms, such as 1,3-dibromo-5,5-dimethyl-hydantoin;

(b) dry hydrogen chloride or calcium bromide;

(c) aliphatic hydrocarbon containing chlorine, bromine or chlorine and bromine, such as tetrabromomethane or bromotrichloromethane, or chlorinated or brominated polybutene;

(d) acetyl bromide, bromacetyl bromide, benzoyl bromide, N-bromo succinimide, or mixtures thereof; and (e) alpha-bromo dialkyl ketone having in addition to the keto-carbonyl carbon atom up to a total of twenty carbon atoms, alpha-dibromo-substituted alkyl diketone wherein its two-keto-carbonyl carbon atoms are in a chain of from 4 to 22 carbon atoms and each bromo-substituent is on a chain carbon atom adjacent to a keto-carbonyl carbon atom, or alpha-bromo aceto-phenone or napthone, or $C_1$-$C_{10}$ dialkyl acetal of alpha-bromo acetaldehyde which additive has a normal boiling point in the range of from about 40° C to about 225° C., such as 1,4-dibromo-2,3-butanedione.

The especially preferred "tar and side product suppressing additives" are N-bromosuccinimide, bromotrichloromethane, N-bromoacetamide and 1,3-dibromo-5,5-dimethylhydantoin. Other preferred additives are α-bromoacetophenone, and 1,4 dibromo-2,3-butanedione. Two or more side product suppressants may be used. For example, it is preferred to use phenothiozine in conjunction with another "additive".

Often it is desirable to minimize the contamination of the substituted anhydride product with the "tar and side product suppressing additive" or its reaction decomposition products. This can be achieved by using a "tar and side product suppressing additive" which can/or whose reaction decomposition products can be removed by distillation at a pressure of 5 to 760 mm Hg. To be most readily removable with unreacted unsaturated anhydride, the side product suppressant or its reaction decomposition products should have a boiling point between 40-300° C at atmospheric pressure.

The "tar and side product suppressing additive" may be introduced into the reaction zone by being mixed with the other reactants or by separate addition, so long as the additive is present during the reaction between the anhydride and the polymer.

The reaction between polymeric alkenes and intramolecular anhydrides of mono unsaturated aliphatic dicarboxylic acids for the addition reaction producing alkenyl-substituted saturated anhydride can be conducted in a batchwise or continuous manner in a stirred-tank type autoclave or equivalent reaction vessle providing intimate contact between the reactants. For batchwise operation the reactants are charged to the closed reaction vessel. The reaction charge comprises propene or butene polymer, unsaturated anhydride and 5 to 200 ppm based on alkenyl material of "tar and side product suppressing additive". The "tar and side product suppressing additive" concentration may be higher but usually higher concentration gives no further advantages. The molar ratio of maleic anhydride to polymer is in the range of 0.7 to 10, preferably from 0.8 to 5. The reactants can be at ambient temperature but the polybutene reactant is usually at an elevated temperature to reduce the time for the reaction mixture to reach reaction temperature. Solid anhydride reactant can be charged alone or dispersed in the polybutene or alone as a melt. The reaction mixture is stirred while being heated to reaction temperature of 150° C to 300° C and during the reaction.

Continuous conduct of the addition reaction is maintained by charging to the reaction vessel containing the stirred adduct forming reaction mixture a melt of the anhydride reactant and preheated polymeric alkene so that their combined heat supplies the heat input needed during reaction.

Reaction time batchwise operation is, in general, 3-20 hours. Continuous operation requires, in general, a shorter residence time, for example 1-3 hours.

Unreacted anhydride is removed from the product alkenyl anhydride by distillation. In some cases, higher boiling additives and their reaction decomposition products will remain in the reaction mix and not be distilled off with the unreacted anhydride. Because it may be desirable to minimize contamination of the product, the "tar and side product suppressing additive" or its reaction decomposition products preferably have sufficiently low boiling points so that they are also removed from the product by distillation. In this preferred case, both unreacted anhydride and additive or its decomposition products, will be distilled off together from the reaction mixture. The mixture of recovered anhydride and "tar and side product suppressing additive" or its decomposition products can be condensed and at least a portion of it is returned to a reaction zone for further reaction with polymeric alkene. The recovered mixture may be reacted with polymeric alkene with or without the addition of fresh anhydride. In some cases the additive or its decomposition products may be separated from the unreacted anhydride before recycling the unreacted anhydride. However, the "tar and side product suppressing additive" or its reaction decomposition products are generally not separated from the recovered anhydride. For example, the reactor charge could be polymeric alkene and a mixture of fresh anhydride plus some of the recovered anhydride and recovered additive and decomposition products from a previous reaction. Another possibility would be to charge a reactor with polymeric alkene and only recovered anhydride and recovered additive and decomposition products. Additional "tar and side product suppressing additive" can be added to maintain an effective level in the reaction zone of from 5 to 200 ppm based on polymeric alkene.

The use of the present invention process and the benefits to be derived therefrom in addition reactions with the before mentioned unsaturated anhydrides will now be illustrated using maleic anhydride, the most commonly, commercially used of those anhydride reactants. Examples 1-6 are conducted with about 0.01 mole of each reactant with a polybutene to maleic anhydride molar ratio of 1.0:1.1. The polybutene used has a 914 $\overline{M}_n$, with 54 ppm chloride (derived from polymerization catalyst). The small scale reactivity screening test used a 11 ml volume Parr bomb with a magnetic stirrer. In each illustrative example 10.0 grams of polybutene and about 1.1 grams of powdered maleic anhydride (MA) were reacted. Polymer/MA mole ratio of 1.0:1.1 are charged at ambient temperature to the bomb. Air is displaced from the bomb with nitrogen gas, the bomb is sealed, the sealed bomb immersed in a 254° C oil bath, the reaction mixture is stirred for six hours, and then sampled.

A larger scale reactor was used in the same maleic anhydride polybutene reaction to produce a sufficient amount of recovered maleic anhydride to use as feed in the smaller Parr reactor. This larger scale reactor employs an autoclave having a dual-impeller, motor driven stirrer, automatic heat control and means for sampling the reaction product before its discharge from the autoclave. The reaction conditions were similar to those used in the small scale test. The condensation reaction was conducted at a temperature of 243°-247° C. After the reaction period, excess maleic anhydride was stripped off, condensed, and saved for further use in the small unit. The polybutene succinic anhydride product was recovered.

A weight aliquot portion of each reaction product from the small scale reactivity unit was chromatographed on silica gel column. The unreacted polybutene was eluted from the column with hexane. The amount of such eluted polymer was determined gravimetrically to obtain the weight percent of polybutene reacted with MA. The total tarry product produced was weighed and its weight percent of total charge (polymer plus MA) calculated.

In the following tables, indentification of the maleic anhydride, the "additive" and concentration thereof in ppm by weight based on polybutene, yield percent and total tar from the small scale reactivity unit are presented.

In Example I, fresh maleic anhydride was used as a reactant in the small reactivity unit. In Example 2, first fresh maleic anhydride was used as a reactant in the autoclave reactor and the unreacted maleic anhydride recovered. This recovered maleic anhydride was then used as a reactant in the small reactivity unit.

| Example | Maleic Anhydride | Additive | Additive Conc. (ppm) | Yield % | Tar % |
|---|---|---|---|---|---|
| 1 | Fresh | None | — | 63.3 | 1.30 |
| 2 | Recycle | None | — | 58.8 | 1.08 |

In comparative Examples 1 and 2, it can be seen that use of recycled maleic anhydride causes a sharp decrease in product yield.

In Examples 3–6, maleic anhydride and polybutene were reacted in the autoclave reactor in the presence of a "tar and side product suppressing additive". The unreacted maleic anhydride was recovered and used as a reactant in the small reactivity unit without further addition of "tar and side product suppressing additive."

| Example | Maleic Anhydride | Additive | Additive Conc. (ppm) | Yield % | Tar % |
|---|---|---|---|---|---|
| 3 | Recycle | BrCl$_3$C | 100 | 64.0 | 0.45 |
| 4 | Recycle | Chlorinated + Brominated polybutene | 112(Cl) 15(Br) | 62.7 | 0.65 |
| 5 | Recycle | N-bromo succinimide | 112 | 68.2 | 0.32 |
| 6 | Recycle | C Br$_4$ | 50 | 62.4 | 0.98 |

The yields attained through the use of "tar and side product suppressing additives" and recycled maleic anjydride are higher than when the additives are not used. In some cases, the yields attained through the use of "tar and side product suppressing additives" and recycled maleic anhydride are higher than when fresh maleic anhydride was used without "tar and side product suppressing additives".

The foregoing examples illustrate how the present process reduces the formation of tar and undesirable side products and increases the product yield. This process not only improves yield and increases plant capacity, but also reduces the amount of anhydride waste by recycling at least a portion of the unreacted anhydride.

The use of other polybutenes and polypropenes in the $\overline{M}_n$ range of about 200 to 3000 can be used in a process affording yield improvement and tarry material suppression in the manner and nature above illustrated for the maleic anhydride reactions. Similar benefits can be expected by the use of the present process with other before-named unsaturated anhydrides of aliphatic dicarboxylic acids.

In tests similar to the Parr bomb tests previously described, a number of additives were tested for their ability to suppress the formation of tar and side products and to increase the yield of substituted succinic anhydride. Those additives below which are effective "tar and side product suppressing additives" would be effective in the recycle process described herein. Polybutenes from two different sources, A and B, were used in the tests.

THE EFFECT OF ADDITIVES ON THE PARR BOMB TEST RESULTS OF POLYBUTENES

| Example | Poly-Butene | Additive Name | Conc., ppm | PBSA Yield[1] Mole % | Tar[1] Wt. % |
|---|---|---|---|---|---|
| 7 | A | None (blank) | — | 65.1 | 1.1 |
| 8 | B | None (blank) | — | 63.3 | 1.3 |
| 9 | A | Hexachloropropene | 150 | 72.4 | 0.6 |
| 10 | A | Tetrachloroethylene | 115 | 64.3 | 1.4 |
| 11 | B | Hexachloroethane | 100 | 64.4 | 1.1 |
| 12 | B | Hexabromoethane | 70 | 70.9 | 0.6 |
| 13 | A | 1,3-Dibromopropane | 100 | 68.5 | 1.4 |
| 14 | B | Chlorinated Polybutene | 100* | 70.3 | 0.4 |
| 15 | B | Brominated Polybutene | 29* | 71.5 | 0.4 |
| 16 | A | Hydrochlorinated Polybutene | 90* | 69.8 | 0.4 |
| 17 | B | Tetrabromomethane | 150 | 75.1 | 0.4 |
| 18 | B | Carbon Tetrabromide | 50 | 72.0 | 0.6 |
| 19 | B | Bromoform | 50 | 72.7 | 0.6 |
| 20 | B | Hexachlorobenzene | 100 | 62.5 | 1.1 |
| 21 | B | 2,5-Dibromothiophene | 55 | 63.5 | 1.2 |
| 22 | A | Bromotrichloromethane | 100 | 72.7 | 0.4 |
| 23 | B | Benzyl Bromide | 58 | 67.9 | 0.3 |
| 24 | A | Sebacyl Chloride | 150 | 72.8 | 0.6 |
| 25 | A | Trichloroacetic acid | 100 | 69.7 | 0.9 |
| 26 | B | Acetyl Bromide | 48 | 74.0 | 0.2 |
| 27 | B | 2-Bromostearic Acid | 98 | 68.8 | 0.6 |
| 28 | B | 1,4-Dibromo-2,3-butanedione | 73 | 76.5 | 0.2 |
| 29 | B | Benzoyl Bromide | 94 | 72.5 | 0.2 |
| 30 | B | α-Bromoacetophenone | 76 | 72.4 | 0.2 |
| 31 | B | α-Chloroacetophenone | 151 | 62.6 | 1.2 |
| 32 | B | p-Toluene Sulfonyl Chloride | 102 | 67.5 | 1.0 |
| 33 | B | N-Bromosuccinimide | 75 | 73.3 | 0.1 |
| 34 | B | N-Chlorosuccinimide | 149 | 70.8 | 0.3 |
| 35 | B | Dibromantin (1,3-dibromo-5,5-dimethyl-hydantoin) | 120 | 73.0 | 0.2 |
| 36 | B | N-Bromoacetamide | 100 | 73.9 | 0.1 |
| 37 | B | Tribromoacetic Acid | 162 | 62.5 | 1.8 |
| 38 | A | Trichloroacetic Acid | 100 | 69.7 | 0.9 |
| 39 | A | 2,6-Di-tert-Butyl Phenol | 150 | 62.3 | 1.8 |

THE EFFECT OF ADDITIVES ON THE PARR BOMB TEST RESULTS OF POLYBUTENES -continued

| Example | Poly-Butene | Additive Name | Conc., ppm | PBSA Yield[1] Mole % | Tar[1] Wt. % |
|---|---|---|---|---|---|
| 40 | A | Methylene-bis-(2,6-Di-tert-Butyl Phenol) | 150 | 53.2 | 3.0 |
| 41 | B | Hydroquinone | 157 | 65.6 | 1.2 |
| 42 | B | Dicyanohydroquinone | 100 | 63.2 | 1.1 |
| 43 | A | Phenothiazine | 150 | 70.1 | 0.1 |
| 44 | B | 2-Chlorophenothiazine | 100 | 66.2 | 0.6 |
| 45 | B | 2-(Trifluoromethyl) Phenothiazine | 75 | 65.1 | 0.3 |
| 46 | B | Thionine | 96 | 62.8 | 1.2 |
| 47 | B | Biphenyl | 100 | 62.0 | 1.5 |
| 48 | B | Carbazole | 130 | 63.5 | 1.3 |
| 49 | B | Tetracyanoethylene | 100 | 60.7 | 1.0 |
| 50 | B | Benzothiazole | 125 | 66.2 | 1.2 |
| 51 | A | Sodium Chloride | 6 | 59.4 | 1.6 |
| 52 | A | Sodium Sulfate | 7 | 56.6 | 2.3 |
| 53 | A | Antimony Trichloride | 6 | 63.3 | 1.3 |
| 54 | B | Aluminum Chloride | 60 | 66.2 | 0.9 |
| 55 | B | Calcium Bromide | 100 | 70.2 | 0.5 |
| 56 | B | Iodine | 75 | 70.0 | 0.4 |
| 57 | B | Iodine Monochloride | 72 | 71.8 | 0.3 |
| 58 | B | Sulfur | 33 | 43.7 | 2.5 |

*In these cases, the ppm concentration refers to the halogen and not to the additive.

As can be seen, a wide variety of materials function to suppress tar formation and/or to improve the yield of polybutene succinic anhydride (PBSA).

We claim:

1. A process for preparing alkenyl-substituted anhydrides by reacting polymers of propene or butene characterized by a number average molecular weight in the range of 200 to 3000 with an intramolecular anhydride chosen from a group consisting of maleic anhydride, citraconic anhydride, itaconic anhydride, ethylmaleic anhydride or halomaleic anhydride, at a mole ratio of 0.8 to 10 of said anhydride to said polymer at a temperature from about 150° C. to about 300° C., which process comprises adding 5-200 ppm based on polymer of a tar and side product suppressing additive to a reaction zone so that the additive is present during the reaction between the polymer and the anhydride, distilling off and condensing unreacted anhydride from the reaction mixture, and returning at least a portion of the recovered anhydride for reaction with said polymer wherein said additive is selected from a group consisting of 1,3-dibromo-5,5-dialkyl substituted hydroantoin whose alkyl-substituents have a total of 2 to 21 carbon atoms, tetra bromomethane, bromotrichloromethane, acetyl bromide, bromoacetyl bromide, benzoyl bromide, N-bromo succinimide, dry hydrogen chloride, calcium bromide and N-bromo-acetamide.

2. The process of claim 1 wherein the additive comprises 1,3-dibromo-5,5-dialkyl-substituted hydantoin wherein the alkyl-substituents have a total of 2 to 21 carbon atoms.

3. The process of claim 2 wherein the additive comprises 1,3-dibromo-5,5-dimethylhydantoin.

4. The process of claim 1 wherein the additive comprises dry hydrogen chloride or calcium bromide.

5. The process of claim 1 wherein the additive comprises tetrabromomethane or bromotrichloromethane.

6. The process of claim 1 wherein said additive comprises acetyl bromide, bromacetyl bromide, benzoyl bromide, N-bromo succinimide, or mixtures thereof.

7. The process of claim 1 wherein the additive is selected from the group consisting of bromotrichloromethane, N-bromo succinimide, 1,3dibromo 5,5-dimethyl hydantoin and N-bromoacetamide.

8. A process for preparing alkenyl-substituted anhydrides by reacting polymers of propene or butene characterized by a number average molecular weight in the range of 200 to 3000 with an intramolecular anhydride chosen from a group consisting of maleic anhydride, citraconic anhydride, itaconic anhydride, ethylmaleic anhydride or halomaleic anhydride, at a mole ratio of 0.8 to 10 of said anhydride to said polymer at a temperature from about 150° C. to about 300° C., which process comprises adding 5-200 ppm based on polymer of a tar and side product suppressing additive to a reaction zone so that the additive is present during the reaction between the polymer and the anhydride, distilling off and condensing unreacted anhydride from the reaction mixture, and returning at least a portion of the recovered anhydride for reaction with said polymer wherein said additive comprises alpha-bromo dialkyl ketone having in addition to the keto-carbonyl carbon atom up to a total of twenty carbon atoms, alpha-dibromo-substituted alkyl diketone wherein its two keto-carbonyl carbon atoms are in a chain of from 4 to 22 carbon atoms and each bromo-substituent is on a chain carbon atom adjacent to a keto-carbonyl carbon atom, or alpha-bromo aceto-phenone or napthone, or $C_1$-$C_{10}$ dialkyl acetal of alpha-bromo acetaldehyde which additive has a normal boiling point in the range of from about 40° C. to about 225° C.

9. The process of claim 8 wherein said additive comprises 1,4-dibromo-2,3-butanedione.

* * * * *

UNITED STATES PATENT OFFICE
CERTIFICATE OF CORRECTION

Patent No. 4,086,251　　　　　　　　　　　Dated April 25, 1978

Inventor(s) Cengel, John A.; and Puskas, Imre

It is certified that error appears in the above-identified patent and that said Letters Patent are hereby corrected as shown below:

| Patent Column | Line | |
|---|---|---|
| 2 | 62 | "sources thereof" should be--sources therefor-- |
| 3 | 57 | "herein produce" should be--herein produces-- |
| 4 | 37 | "is useful" should be--is a useful-- |
| 4 | 66 | "3,954,812," should be--3,954,812;-- |
| 5 | 3 | "NO. 3,960,900" should be--No. 3,960,900-- |
| 6 | 31 | "acetyl dehyde" should be--acetyldehyde-- |
| 6 | 40 | "halogen chloride" should be--hydrogen chloride-- |
| 7 | 32 | "vessle" should be--vessel-- |
| 8 | 27 | "invention process" should be--inventive process-- |
| 9 | 35 | "anjyride" should be--anhydride-- |
| 10 | 28 | "76.5" should be--75.5-- |
| 11 | 46 | "hydroantoin" should be--hydantoin-- |

Signed and Sealed this

Thirty-first Day of October 1978

[SEAL]

Attest:

RUTH C. MASON
Attesting Officer

DONALD W. BANNER
Commissioner of Patents and Trademarks